United States Patent
Smith et al.

(10) Patent No.: US 9,430,127 B2
(45) Date of Patent: Aug. 30, 2016

(54) SYSTEMS AND METHODS FOR PROVIDING FEEDBACK CUES FOR TOUCH SCREEN INTERFACE INTERACTION WITH CHEMICAL AND BIOLOGICAL STRUCTURE DRAWING APPLICATIONS

(71) Applicant: CambridgeSoft Corporation, Waltham, MA (US)

(72) Inventors: Robin Y. Smith, Boston, MA (US); Hans Keil, Natick, MA (US)

(73) Assignee: CambridgeSoft Corporation, Waltham, MA (US)

( * ) Notice: Subject to any disclaimer, the term of this patent is extended or adjusted under 35 U.S.C. 154(b) by 303 days.

(21) Appl. No.: 13/890,133

(22) Filed: May 8, 2013

(65) Prior Publication Data

US 2014/0337725 A1    Nov. 13, 2014

(51) Int. Cl.
*G06F 3/0484* (2013.01)
*G06F 3/01* (2006.01)
*G06F 3/0488* (2013.01)
*G06F 19/26* (2011.01)
*G06F 19/00* (2011.01)

(52) U.S. Cl.
CPC ............ *G06F 3/0484* (2013.01); *G06F 3/016* (2013.01); *G06F 3/0488* (2013.01); *G06F 19/26* (2013.01); *G06F 19/708* (2013.01)

(58) Field of Classification Search
CPC .... G06F 19/26; G06F 19/708; G06F 19/701; G06F 19/702; G06F 3/0488; G06F 3/0484; G06F 3/016
See application file for complete search history.

(56) References Cited

U.S. PATENT DOCUMENTS 4,967,372 A * 10/1990 Feldman ..................... 715/203
5,249,137 A     9/1993 Wilson et al.
(Continued)

FOREIGN PATENT DOCUMENTS

EP    1526471 A1    4/2005
EP    2567338 A1    3/2013
(Continued)

OTHER PUBLICATIONS

"Van Der Weals Radius of the elements", retrieved from http://periodictable.com/Properties/A/VanDerWaalsRadius.v.html, May 22, 2008.*

(Continued)

*Primary Examiner* — Li Sun
(74) *Attorney, Agent, or Firm* — Choate, Hall & Stewart—LLP; William R. Haulbrook

(57) ABSTRACT

Creating a graphical representation of at least one of a chemical structure and a biological structure using a touch screen interface may include identifying connection location (s) of an in-progress structure and connection location(s) of a separate structure element, determine, upon receipt of a gesture input moving the structure element towards the in-progress structure, that a distance between a first connection location of the in-progress structure and a first connection location of the structure element signals an intended connection of the structure element to the in-progress structure at or about the corresponding connection locations, analyze a resultant structure formed by connection of the in-progress structure and the structure element at or about the corresponding connection locations to determine a response, and provide a visible cue, an audible cue, and/or a haptic cue corresponding to the response.

21 Claims, 6 Drawing Sheets

(56) References Cited

U.S. PATENT DOCUMENTS

| | | | |
|---|---|---|---|
| 5,386,507 A * | 1/1995 | Teig et al. .................. 715/836 | |
| 5,434,971 A | 7/1995 | Lysakowski, Jr. | |
| 5,461,580 A | 10/1995 | Facci et al. | |
| 6,017,390 A * | 1/2000 | Charych et al. ............. 117/68 | |
| 6,304,869 B1 | 10/2001 | Moore et al. | |
| 6,434,490 B1 * | 8/2002 | Agrafiotis et al. ........... 702/27 | |
| 7,250,950 B2 | 7/2007 | Smith et al. | |
| 7,613,574 B2 | 11/2009 | Verseput | |
| 7,650,327 B2 | 1/2010 | Remsen et al. | |
| 7,663,607 B2 | 2/2010 | Hotelling et al. | |
| 7,676,499 B2 | 3/2010 | Dorsett, Jr. | |
| 7,705,830 B2 | 4/2010 | Westerman et al. | |
| 7,707,206 B2 | 4/2010 | Encina et al. | |
| 7,805,437 B1 | 9/2010 | Andersson et al. | |
| 8,407,578 B2 | 3/2013 | Boyer et al. | |
| 8,433,723 B2 | 4/2013 | Smith et al. | |
| 8,538,983 B2 | 9/2013 | Huang et al. | |
| 2002/0049548 A1 | 4/2002 | Bunin | |
| 2002/0107359 A1 | 8/2002 | Hogarth et al. | |
| 2002/0161599 A1 | 10/2002 | Faerman et al. | |
| 2003/0194687 A1* | 10/2003 | Clark .......................... 434/278 | |
| 2004/0003000 A1 | 1/2004 | Smith et al. | |
| 2004/0006742 A1 | 1/2004 | Slocombe | |
| 2004/0024493 A1 | 2/2004 | Fagrell et al. | |
| 2004/0122641 A1 | 6/2004 | Miller et al. | |
| 2004/0236740 A1 | 11/2004 | Cho et al. | |
| 2004/0249791 A1 | 12/2004 | Waters et al. | |
| 2005/0094205 A1* | 5/2005 | Lo et al. ..................... 358/1.18 | |
| 2005/0102313 A1 | 5/2005 | Levering et al. | |
| 2005/0123993 A1* | 6/2005 | Brunner et al. .............. 435/7.1 | |
| 2005/0131894 A1 | 6/2005 | Vuong | |
| 2005/0177280 A1 | 8/2005 | Almstetter et al. | |
| 2005/0226495 A1 | 10/2005 | Li | |
| 2006/0061595 A1 | 3/2006 | Goede et al. | |
| 2006/0123113 A1 | 6/2006 | Friedman | |
| 2006/0277201 A1 | 12/2006 | Dorsett | |
| 2007/0016853 A1 | 1/2007 | Abagyan et al. | |
| 2007/0174765 A1 | 7/2007 | Schleppenbach et al. | |
| 2007/0177803 A1 | 8/2007 | Elias et al. | |
| 2007/0192747 A1 | 8/2007 | Phelan et al. | |
| 2007/0260583 A1 | 11/2007 | Domine et al. | |
| 2008/0036743 A1 | 2/2008 | Westerman et al. | |
| 2008/0136785 A1* | 6/2008 | Baudisch et al. ............ 345/173 | |
| 2008/0140616 A1 | 6/2008 | Encina et al. | |
| 2008/0165140 A1 | 7/2008 | Christie et al. | |
| 2008/0213663 A1* | 9/2008 | Hu et al. ..................... 429/219 | |
| 2008/0228774 A1 | 9/2008 | Hamilton et al. | |
| 2008/0309632 A1 | 12/2008 | Westerman et al. | |
| 2009/0006411 A1 | 1/2009 | Lele et al. | |
| 2009/0063427 A1 | 3/2009 | Zuta et al. | |
| 2009/0171975 A1 | 7/2009 | McConnell et al. | |
| 2009/0273571 A1 | 11/2009 | Bowens | |
| 2010/0257457 A1 | 10/2010 | De Goes | |
| 2011/0163944 A1 | 7/2011 | Bilbrey et al. | |
| 2011/0221656 A1 | 9/2011 | Haddick et al. | |
| 2011/0276589 A1 | 11/2011 | Smith et al. | |
| 2012/0019488 A1 | 1/2012 | McCarthy | |
| 2012/0078853 A1 | 3/2012 | Huang et al. | |
| 2012/0110486 A1 | 5/2012 | Sirpal et al. | |
| 2012/0154440 A1 | 6/2012 | Nicholls et al. | |
| 2012/0173622 A1 | 7/2012 | Toledano et al. | |
| 2012/0188147 A1 | 7/2012 | Hosein et al. | |
| 2012/0246228 A1 | 9/2012 | Udezue et al. | |
| 2012/0284638 A1 | 11/2012 | Cutler et al. | |
| 2012/0311038 A1 | 12/2012 | Trinh et al. | |
| 2012/0324368 A1 | 12/2012 | Putz et al. | |
| 2013/0044042 A1 | 2/2013 | Olsson et al. | |
| 2013/0061163 A1* | 3/2013 | Clark et al. ................... 715/771 | |
| 2013/0218878 A1 | 8/2013 | Smith et al. | |
| 2013/0222265 A1 | 8/2013 | Smith et al. | |
| 2014/0089329 A1* | 3/2014 | Kozloski et al. ............. 707/749 | |
| 2014/0267240 A1 | 9/2014 | Smith | |
| 2014/0282106 A1 | 9/2014 | Smith et al. | |
| 2015/0112604 A1 | 4/2015 | Smith | |

FOREIGN PATENT DOCUMENTS

| | | |
|---|---|---|
| GB | 2493830 A | 2/2013 |
| WO | WO-2007092842 A2 | 8/2007 |
| WO | WO-2011140148 A1 | 11/2011 |
| WO | WO-2013126077 A1 | 8/2013 |

OTHER PUBLICATIONS

International Search Report, PCT/US2012/026574, dated Mar. 20, 2013, 4 pgs.

Kim, et al, Development of a Gesture-Based Molecular Visualization Tool Based on Virtual Reality for Molecular Docking, Bull. Korean Chem. Soc. 2004, vol. 25, No. 10 pp. 1571-1574.

Williams, et al., Mobile apps for chemistry in the world of drug discovery, Drug Discovery Today, vol. 16. Nos. 21/22, Nov. 2011, pp. 928-939.

Williams, et al, Smart Phones, a Powerful Tool in the Chemistry Classroom, Journal of Chemical Education, 2011, pp. 683-686.

Wobbrock et al, User-Defined Gestures for Surface Computing, CHI—Tabletop Gestures, Apr. 7, 2009, pp. 1083-1092.

Written Opinion, PCT/US2012/026574, dated Mar. 20, 2013, 8 pgs.

Algorri et al. "Reconstruction of Chemical Molecules from Images," 2007 Annual International Conference of the IEEE Engineering in Medicine and Biology Society (EMBC '07), Lyon, France, Aug. 22-26, 2007, in Conjunction with the Biennial Conference of the Societe Francaise de Genie Biologique et Medical (SFGB), Aug. 22, 2007, pp. 4609-4612.

Casey et al. "Optical Recognition of Chemical Graphics," Document Analysis and Recognition, 1993, Proceedings of the Second International Conference on, Tsukuba Science City, Japan, Oct. 20-22, 1993, Los Alamitos, CA, USA, IEEE Comput. Soc., Oct. 20, 1993, pp. 627-631.

Filippov et al. "Optical Structure Recognition Software to Recover Chemical Information: OSRA, An Open Source Solution," Journal of Chemical Information and Modeling, vol. 49, No. 3, Mar. 23, 2009, pp. 740-743.

Park et al. "Automated extraction of chemical structure information from digital raster images," Chemistry Central Journal, Biomed Central Ltd., vol. 3, No. 1, Feb. 5, 2009, pp. 1-16.

Valko et al. "CLiDE Pro: The Latest Generation of CLiDE, a Tool for Optical Chemical Structure Recognition," Journal of Chemical Information and Modeling, vol. 49, No. 4, Mar. 19, 2009, pp. 780-787.

https://itunes.apple.com/nl/app/flick./id644265534?mt=8 (2013).

http://getflick.io/ (2013).

Carmigniani, J. et al., Augmented Reality Technologies, Systems and Applications, Multimedia Tools and Applications 51:341-377, (2011).

Clark A. M., Basic Primitives for Molecular Diagram Sketching, Journal of Cheminformatics 2:8 (2010).

European Search Report for 13275308.8, Apr. 9, 2014, 4 pages.

European Search Report for 13275308.8, Aug. 13, 2014, 8 pages.

Furlon, Rod, Build Your Own Google Glass, Resources Hands on, IEEE Spectrum, IEEE Inc., vol. 50, No. 1, pp. 20-21, (Jan. 1, 2013).

Giudice N. A. et al., Learning Non-Visual Graphical Information Using a Touch-Based Vibro-Audio Interface, Proceedings of the 14th International ACM Sigaccess Conference on Computers and Accessibility, Assets '12, 103-110 (Jan. 1, 2012).

International Search Report for PCT/US2014/016249, Aug. 13, 2014, 4 pages.

International Search Report for PCT/US2014/035685, Aug. 4, 2014, 4 pages.

Li et al., Personal Experience with Four Kinds of Chemical Structure Drawing Software: Review on ChemDraw, ChemWindow, ISIS/Draw, and ChemSketch, J. Chem. Inf. Comput. Sci. 44:1886-1890 (2004).

Shine et al., ChemPad3 a tutorial, May 21, 2008, 10 pages.

Toennies J. L. et al., Toward Haptic/Aural Touchscreen Display of Graphical Mathematics for the Education of Blind Students, WHC, IEEE, 373:378 (2011).

Written Opinion for PCT/US2014/016249, Aug. 13, 2014, 7 pages.

Written Opinion for PCT/US2014/035685, Aug. 4, 2014, 8 pages.

(56) References Cited

OTHER PUBLICATIONS

Australian Patent Application No. 2011248243, APO Examination Report No. 1, issued Nov. 5, 2013, 3 pages.
Bennett, Samsung's AllShare Play pushes pictures from phone to cloud and TV, <http://news.cnet.com/8301-1035_3-57391735-94/samsungs-allshare-play-pushes-pictures-from-phone-to-cloud-and-tv/> [retrieved Oct. 24, 2013], Mar. 6, 2012, 9 pages.
First Office Action for Chinese Application No. 201190000597.X, mailed May 29, 2013, 4 pages Including Translation.
Gonzalez-Villanueva et al., WallShare: A Collaborative Multi-pointer System for Portable Devices, Nov. 19, 2012, 7 pages.
International Search Report for PCT Application No. PCT/US2011/035070, mailed Oct. 6, 2011, 4 pages.
Jurach, T., Microsoft Outlook Quick Start Email Guide!, 1-3 (2006).
Layar, What is Layar?, <http://www.layar.com/features/> [retrieved Nov. 14, 2012], 7 pages.
Lorensen et al., Marching Cubes: A high resolution 3D surface construction algorithm. In: Computer Graphics, vol. 21, Nr. 4, Jul. 1987.
Lucero et al., Pass-Them-Around: Collaborative Use of Mobile Phones for Photo Sharing, CHI 2011—Session: Photo Sharing, May 7-11, 2011, Vancouver, BC, Canada, 10 pages.
Park et al. Tunable Machine Vision-Based Strategy for Automated Annotation of Chemical Databases, Journal of Chemical Information and Modeling, vol. 49, No. 8, 2009, pp. 1993-2001.
Pering et al., Enabling Pervasive Collaboration with Platform Composition, Intel Research Santa Clara, 2009, 18 pages.
Pering et al., Spontaneous Marriages of Mobile Devices and Inter-active Spaces, Communications of the ACM, Sep. 2005, vol. 48, No. 9, pp. 53-59, 7 pages.
Scheible et al., MobiToss: A Novel gesture based interface for creating and sharing mobile multimedia art on large public displays, MM'08, Oct. 26-31, 2008 Vancouver British Columbia, Canada, pp. 957-960, 4 pages.
Tsotsis, Word Lens Translates Words Inside of Images. Yes Really., <http://techcrunch.com/2010/12/16/world-lens-translates-words-inside-of-images-yes-really/> [retrieved Nov. 14, 2012], Dec. 16, 2010, 3 pages.
Weinberg et al., ZooZBeat: a Gesture-based Mobile Music Studio, NIME 2009, pp. 312-315, 4 pages.
Written Opinion for PCT Application No. PCT/US2011/035070, mailed Oct. 6, 2011, 9 pages.
Cambridgesoft, Inc., Chem & Bio Draw, Version 12.0, 24 pages, 2009.
Cambridgesoft, Inc., ChemDraw User's Guide, Version 9.0.1, 23 pages, 2004.
ChemJuice Grande—Basic Structure Drawing, printout page of YouTube video posting from IOBS at http://www.youtube.com/watch?v=mKOcC5bLzdO, <http://www.youtube.com/watch?v=mKOcC5bLzdO>uploaded Oct. 3, 2011, printed May 18, 2015, 2 pages.
IDBS Makes Chemical Structure Drawing Mobile, Press Release, ID Business Solutions, Ltd., 2 pages, Dec. 9, 2009.
Logtenberg, Jeroen, Multi-user interaction with molecular visualizations on a multi-touch table, MSc thesis, Human Media Interaction Group, University of Twente, 48 pages, Aug. 11, 2009.
Mills, Nancy, ChemDraw Ultra 10.0, Journal of American Chemical Society, 128(41):13649-13650, 2006.
Mobile Molecular DataSheet, http://molmatinf.com/mmdsios.html, <http://molmatinf.com/mmdsios.html>Molecular Materials Informatics, Inc., Sep. 23, 2011, retrieved by Archive.org as https://web.archive.org/web/20120403140454/http:l/molmatinf.com/mmdsios.html on Apr. 3, 2012, 4 pages.
MolPrime+, http://molmatinf.com/molprimeplus.html, <http://molmatinf.com/molprimeplus.html>Molecular Materials Informatics, Inc., Jan. 23, 2011, 13 pages.

\* cited by examiner

SYSTEMS AND METHODS FOR PROVIDING FEEDBACK CUES FOR TOUCH SCREEN INTERFACE INTERACTION WITH CHEMICAL AND BIOLOGICAL STRUCTURE DRAWING APPLICATIONS

BACKGROUND

Chemical structure, biological sequence, and large molecule rendering software is widely used by research and educational institutions to depict chemical structures, chemical reactions, and biological sequences (including nucleotide and amino acid sequences) of interest. Unlike chemical formulas or chemical names, chemical structure formulas provide a graphical representation of the molecular structure. A graphical chemical structure representation is capable of indicating the arrangements of atoms in a way that a chemical formula cannot. Similarly, large molecules and other biological sequences can be graphically represented in various ways; for example, a biological sequence can be represented textually by a sequence of letters corresponding to nucleotide codes or amino acid codes. Alternatively, a two- or three-dimensional graphical representation may be determined from a nucleotide and/or amino acid sequence to depict the arrangements of atoms, nucleotides, and/or amino acid residues of the biological molecule as a chemical structure, a ball-and-stick model, a ribbon diagram, a space-filling model, or an electrostatic model.

Current methods for drawing and editing biological and chemical structures on a computer utilize mouse-driven or touch pad commands that include pointing and clicking on displayed menu items in a graphical user interface. Existing chemical and biological structure rendering applications for handheld electronic devices such as tablet computers and portable phones utilize the same menu-driven paradigm. These applications can be clumsy and difficult to use for drawing purposes. For example, it may be difficult to identify connections made between elements within a chemical or biological structure drawing because the drag and drop touch screen interface becomes obscured by the hand during gesture-based manipulation of drawing elements.

SUMMARY OF THE INVENTION

Described herein are various embodiments of systems, methods, and apparatus that allow a user to electronically draw and edit a chemical structure while receiving feedback cues related to interaction between biological or chemical structure elements.

In one aspect, the present disclosure relates to a system for creating a graphical representation of at least one of a chemical structure and a biological structure using a touch screen interface, the system including a processor and a memory having a set of instructions stored thereon, where the instructions, when executed, cause the processor to provide a representation of at least a portion of an in-progress structure for presentation on a graphical display of a computing device, identify one or more connection locations of the portion of the in-progress structure, and identify one or more connection locations of a structure element, where the structure element is separate from the in-progress structure. The instructions, when executed, may cause the processor to receive a gesture input upon a touch sensitive portion of the graphical display corresponding to movement of the structure element towards the portion of the in-progress structure, and determine whether a distance between a first connection location of the one or more connection locations of the portion of the in-progress structure and a first connection location of the one or more connection locations of the structure element signals an intended connection of the structure element to the in-progress structure at or about the corresponding connection locations. The instructions, when executed, may cause the processor to, based upon determining the intended connection, analyze a resultant structure formed by connection of the in-progress structure and the structure element at or about the corresponding connection locations of the structure element and the in-progress structure to determine a response, and provide, responsive to analysis, for presentation to a user of the computing device, at least one of a visible cue, an audible cue, and a haptic cue corresponding to the response.

In some embodiments, at least one of i) a strength of the haptic cue, ii) a duration of the haptic cue, iii) a volume of the audible cue, iv) a duration of the audible cue, and v) a tone of the audible cue is selected based at least in part upon the response. At least one of i) a strength of the haptic cue, ii) a duration of the haptic cue, iii) a volume of the audible cue, iv) a duration of the audible cue, and v) a tone of the audible cue may be selected based at least in part upon a number of bonds formed between a) the first connection location of the structure element and b) the first connection location of the in-progress structure. The response may include one of allow, warn, and prevent.

In some embodiments, the response is allow, and the instructions, when executed, cause the processor to cause presentation, within the graphical display, of formation of the resultant structure. The instructions, when executed, may cause the processor to present, to the user, the visible cue of the first connection location of the structure element connecting with the first connection location of the in-progress structure. The visible cue may include a zoom display panel presented upon the graphical display. The visible cue may include a visible indication of a loss of one or more atoms caused by the formation of the resultant structure.

In some embodiments, the instructions, when executed, cause the processor to append the structure element to the in-progress structure at the corresponding connection locations. The instructions, when executed, may cause the processor to replace a portion of the in-progress structure with at least a portion of the structure element at the corresponding connection locations. The instructions, when executed, may cause the processor to merge the structure element into the in-progress structure at the corresponding connection locations.

In some embodiments, the visible cue includes an alteration in at least one of color, brightness, and contrast of at least a portion of the graphical display. Receiving the gesture input may include receiving the gesture input, over a network, from the computing device. The computing device may include the processor.

In one aspect, the present disclosure relates to a method including providing a representation of at least a portion of an in-progress structure for presentation on a graphical display of a computing device, identifying, by a processor of a computing device, one or more connection locations of the portion of the in-progress structure, and identifying, by the processor, one or more connection locations of a structure element, where the structure element is separate from the in-progress structure. The method may include receiving a gesture input upon a touch sensitive portion of the graphical display corresponding to movement of the structure element towards the portion of the in-progress structure, and determining, by the processor, whether a distance between a first connection location of the one or more connection locations of the portion of the in-progress structure and a first connection location of the one or more connection locations of the structure element signals an intended connection of the structure element to the in-progress structure at or about the corresponding connection locations. The method may include, based upon determining the intended connection, analyzing, by the processor, a resultant structure formed by connection of the in-progress structure and the structure element at or about the corresponding connection locations of the structure element and the in-progress structure to determine a response. The method may include providing, responsive to analysis, for presentation to a user of the computing device, at least one feedback cue corresponding to the response, where the feedback cue includes a visible cue, an audible cue, or a haptic cue.

In some embodiments, the feedback cue is selected based at least in part upon at least one of a) a type of the structure element and b) a type of an element of the in-progress structure including the first connection location. The type of the structure element may be a molecule, an atom, or a substituent. The in-progress structure may be a biological sequence. The type of the structure element may be a biological scaffold. The structure element may include one or more nucleotides. The structure element may include at least one an amino acid residue or amino acid.

In one aspect, the present disclosure relates to a non-transitory computer readable medium having instructions stored thereon, where the instructions, when executed by a processor, cause the processor to provide a representation of at least a portion of an in-progress structure for presentation on a graphical display of a computing device, identify one or more connection locations of the portion of the in-progress structure, and identify one or more connection locations of a structure element, where the structure element is separate from the in-progress structure. The instructions, when executed, may cause the processor to receive a gesture input upon a touch sensitive portion of the graphical display corresponding to movement of the structure element towards the portion of the in-progress structure, and determine whether a distance between a first connection location of the one or more connection locations of the portion of the in-progress structure and a first connection location of the one or more connection locations of the structure element signals an intended connection of the structure element to the in-progress structure at or about the corresponding connection locations. The instructions, when executed, may cause the processor to, based upon determining the intended connection, analyze a resultant structure formed by connection of the in-progress structure and the structure element at or about the corresponding connection locations of the structure element and the in-progress structure to determine a response. The instructions, when executed, may cause the processor to provide, responsive to analysis, for presentation to a user of the computing device, at least one of a visible cue, an audible cue, and a haptic cue corresponding to the response.

In some embodiments, the instructions cause the processor to, prior to determining whether the distance between the first connection location of the in-progress structure and the first connection location of the structure element signals the intended connection, for each connection location of the one or more connection locations of the structure element, and for each connection location of the one or more connection locations of the in-progress structure, determine a respective distance between the respective connection location of the structure element and the respective connection location of the in-progress structure, and identify whether the respective distance is within a threshold distance. The threshold distance may be based at least in part upon a type of the in-progress structure. The threshold distance may be based at least in part on one or more of intermolecular forces, intramolecular forces, and van der Waal forces corresponding to one or both of the in-progress structure and the structure element.

BRIEF DESCRIPTION OF THE DRAWINGS

The foregoing and other objects, aspects, features, and advantages of the invention will become more apparent and may be better understood by referring to the following description taken in conjunction with the accompanying drawings, in which.

Figure 1B:
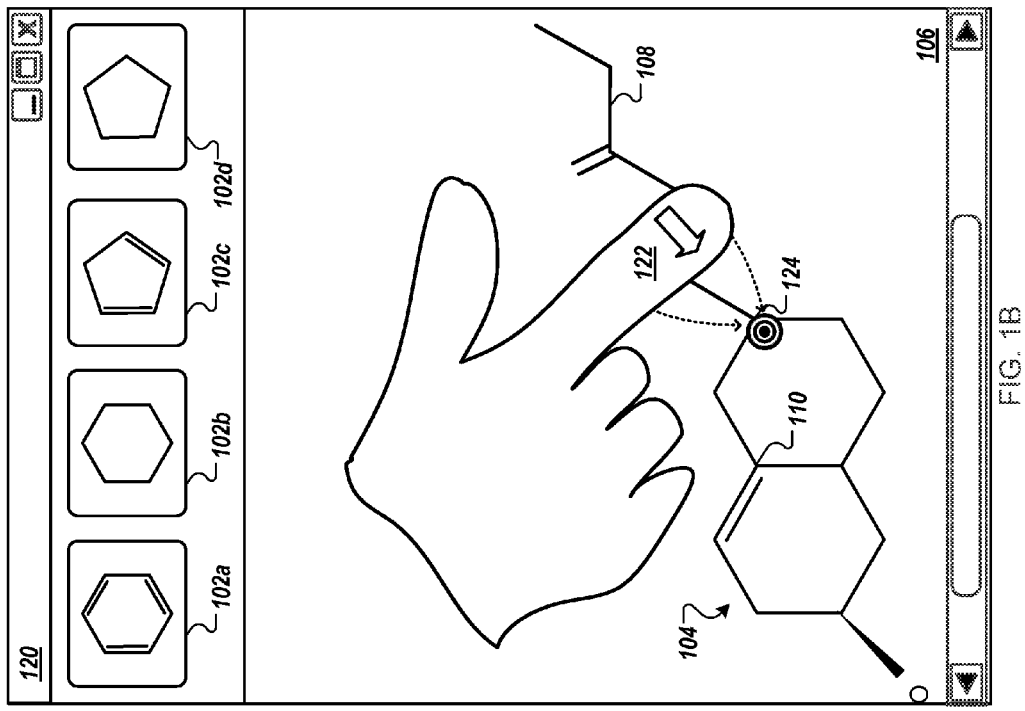
FIGS. 1A and 1B illustrate a series of screen shots depicting a gesture-based addition of an element to an in-progress chemical structure drawing within a utility for creating or editing a graphical representation of a chemical structure.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DESCRIPTION

It is contemplated that apparatus, systems, and methods of the claimed invention encompass variations and adaptations developed using information from the embodiments described herein. Adaptation and/or modification of the apparatus, systems, and methods described herein may be performed by those of ordinary skill in the relevant art.

Throughout the description, where apparatus and systems are described as having, including, or comprising specific components, or where processes and methods are described as having, including, or comprising specific steps, it is contemplated that, additionally, there are apparatus and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

In general, in various embodiments, the present invention pertains to apparatus, systems, and methods for drawing chemical structures on a computing device. The computing device may be, for example, a personal computer, a workstation, a tablet computer (e.g., an Apple® IPad® by Apple Inc. of Cupertino, Calif.), or a mobile phone device. As used herein, the term "molecular scaffold" refers to a portion (e.g., a fragment) of a graphical representation of a chemical structure. As used herein, the term "biological scaffold" refers to a portion (e.g., a fragment) of a graphical representation of a biological structure.

Figure 1A:
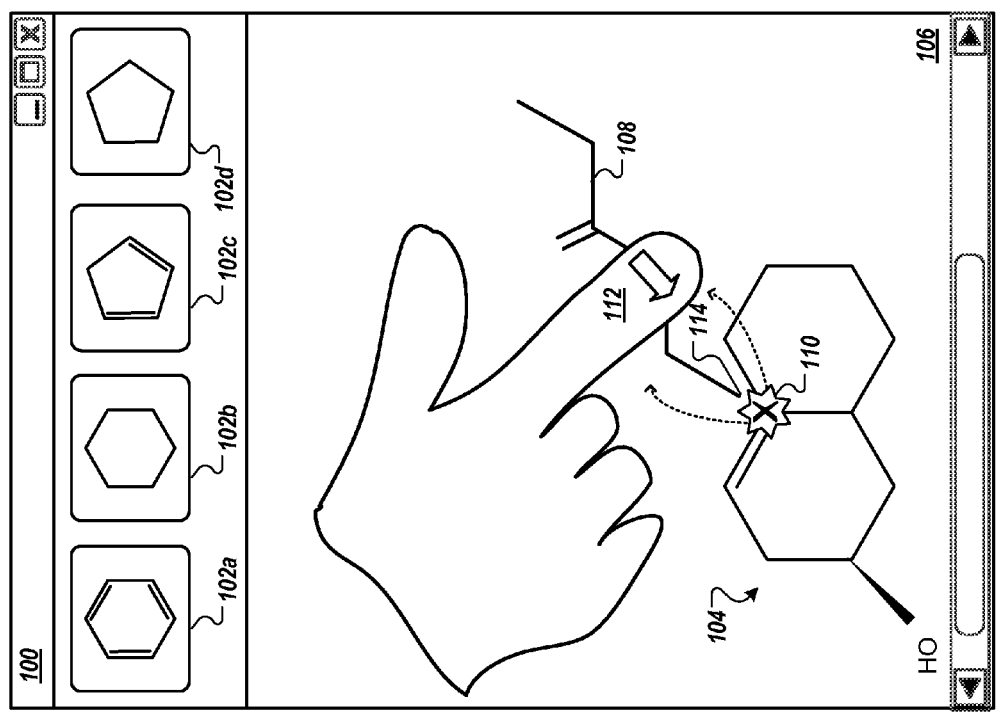

Referring to FIGS. 1A and 1B, a series of screen shots illustrate an example user interface of a utility for creating and/or editing a graphical representation of a chemical structure. The user interface includes a series of editing tools 102 for building a graphical representation of a chemical structure, e.g., a chemical structure 104 presented within an editing pane 106. A user, in some implementations, may select one of the editing tools 102 representing a ring of atoms, a bond, or a substituent, in order to place the selected ring, bond, or substituent in the chemical structure 104. For example, the user may drag and drop the selected feature into the editing pane 106 to add the selected feature at a desired position within or on the in-progress chemical structure 104. In other examples, the user may add to the chemical structure 104 a heteroatom, a ring substituent, a multi-ring substituent, an acyclic chain, a chair cyclohexane, and/or any other molecular component. Additionally, the drawing/editing utility may determine whether or not a given edit would result in a structure that is chemically feasible and may limit executable edits to only those resulting in feasible chemical structures.

In some implementations, the drawing/editing utility provides cues to a user to alert the user regarding execution of edits. For example, while working within a smaller display, such as that of a smart phone or tablet computer, a user may become frustrated due to obscured visibility caused by inputting touch gestures (e.g., a "fat finger" is in the way of reviewing alignment of the selected element with the in-progress chemical structure 104). To provide feedback to the user regarding modifications made to the in-progress chemical structure, the drawing/editing utility may provide one or more of haptic, audible, and visible cues.

Turning to a first screen shot 100 of FIG. 1A, the user has aligned a structure element 108 with a connection location 110 of the in-progress chemical structure 104, and the user is providing a gesture input 112 moving a connection location 114 of the element 108 towards the connection location 110 of the in-progress chemical structure 104. Based upon analysis of a resultant chemical structure created by appending the structure element 108 to the in-progress chemical structure 104 at the connection locations 110 and 114, in some implementations, the drawing/editing utility determines that the connection at the connection locations 110, 114 is not chemically feasible. For example, based upon bond saturation at the connection location 110, the element 108 may be prevented from attaching at the connection location 110 due to steric hindrance. Based upon identification of steric hindrance, the drawing/editing utility may determine that the user should be prevented from adding the structure element 108 to the in-progress chemical structure 104 at the connection location 110. Responsive to this determination, the drawing/editing utility may present feedback cues to the user, such as a haptic cue interfering with the motion of the gesture input 112 towards the connection location 110 (or, alternatively, a vibration), an audible cue (e.g., buzzer, other sound with negative connotation), or a visible cue (e.g., flashing screen, dimming of screen, adjustment of color of screen to a color with negative connotation, such as red, etc.).

Turning to a second screen shoot 120 of FIG. 1B, the user may apply an adjusted gesture movement 122 of the structure element 108 towards the in-progress chemical structure 104 at a second connection location 124. Based upon analysis of a resultant chemical structure created by appending the structure element 108 to the in-progress chemical structure 108 at the connection locations 114 and 124, in some implementations, the drawing/editing utility determines that the connection at the connection locations 114 and 124 is allowable (e.g., chemically feasible). The drawing/editing utility may determine that the user should be allowed to add the structure element 108 to the in-progress chemical structure 104 at the connection location 124. Responsive to this determination, the drawing/editing utility may present feedback cues to the user, such as a haptic cue directed with the motion of the gesture input 112 towards the connection location 110, an audible cue (e.g., bell ding, other sound with positive connotation), or a visual cue (e.g., flashing screen, brightening of screen, adjustment of color of screen to a color with positive connotation, such as green, etc.). In some implementations, the drawing/editing utility, upon determining the user intends to draw connection location 114 towards connection location 124 for appending the two structures, automatically completes the operation such that the structure element 108 is joined with the in-progress chemical structure 104 at the connection location 124.

Figure 2A:
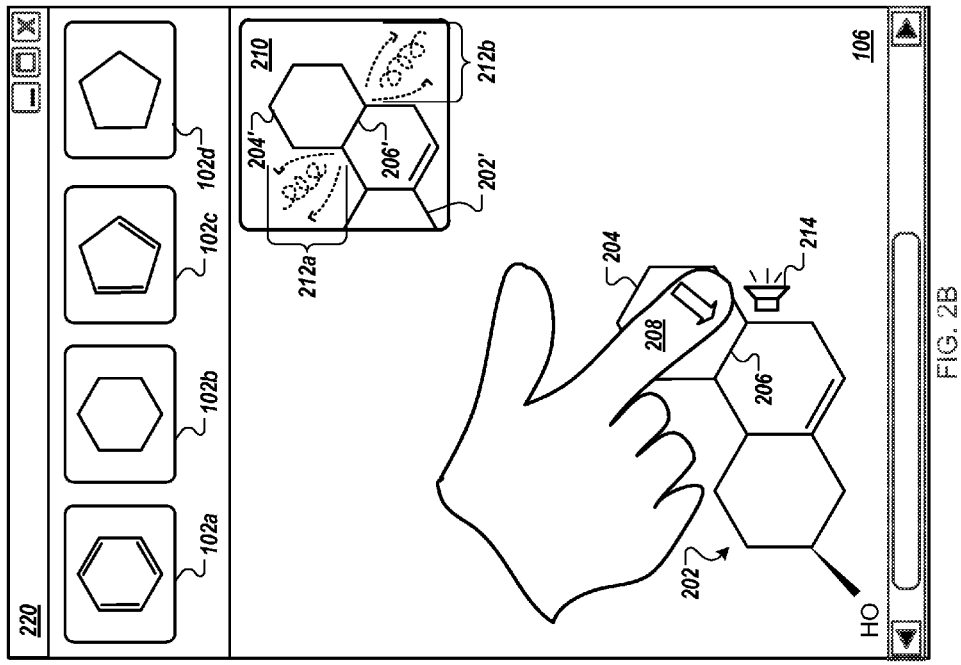
FIGS. 2A and 2B illustrate another series of screen shots depicting a gesture-based addition of an element to an in-progress chemical structure drawing within a utility for creating or editing a graphical representation of a chemical structure.
Figure 2B:
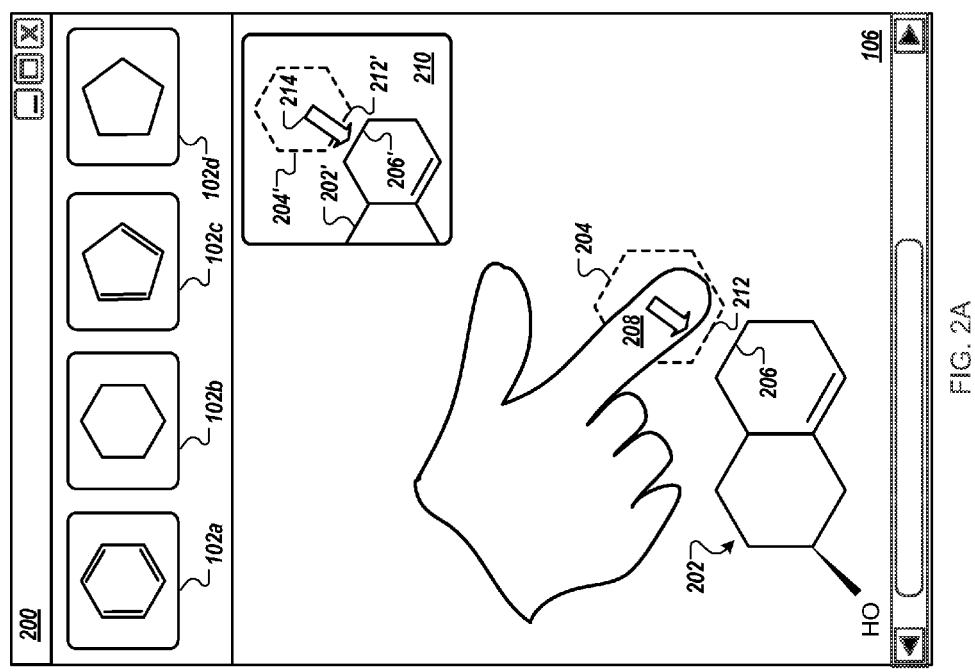

FIGS. 2A and 2B illustrate another series of screen shots depicting a gesture-based addition of a structure element 204 to an in-progress chemical structure 202 within a utility for creating or editing a graphical representation of a chemical structure, such as the utility described in relation to FIGS. 1A and 1B. Within the screen shots of FIGS. 2A and 2B, the user is presented with a visual feedback cue in the form of a zoom pane 210 illustrating a view 204' of structure element 204 as it approaches a portion 202' of the in-progress chemical structure 202 (e.g., at a connection location 206). In some implementations, a position of the zoom pane 210 is based in part upon a position of the structure element 204 (e.g., based on an estimation of a portion of the screen obscured by the user during gesture input). The position of the zoom pane 210, in some implementations, is stationary or semi-stationary (e.g., drag & drop, user-specified, etc.).

Turning to a first screen shot 200 of FIG. 2A, the user may apply a gesture movement 208 of the structure element 204 towards the in-progress chemical structure 202 at the connection location 206. Based upon analysis of a resultant chemical structure created by appending the structure element 204 to the in-progress chemical structure 202 at the connection locations 206 and 212, in some implementations, the drawing/editing utility determines that the connection at the connection locations 206 and 212 is allowable (e.g., chemically feasible). The drawing/editing utility may determine that the user should be allowed to add the structure element 204 to the in-progress chemical structure 202 at the connection location 206. Responsive to this determination, the drawing/editing utility may present feedback cues to the user, such as a visual cue presented within the zoom pane 210 illustrating an arrow 214 moving the view 204' of the element 204 towards the portion 202' at the connection location 206. Additional visual, audio, and/or haptic cue(s) may be supplied to the user as well, such as those described above in relation to FIG. 1B.

Turning to FIG. 2B, in some implementations, upon connection of the structural element 204 with the in-progress chemical structure 202 at the connection location 206, in some implementations, the zoom pane 210 includes a confirming graphic. The zoom pane, in the present example, illustrates an animation representing a loss of atoms 212 (e.g., two carbons 212a and 212b, a group of one carbon and two hydrogens for each of 212a and 212b, etc.) due to the forming of the connection between the connection location 206 and the connection location 212. For example, carbons may be illustrated as spinning away in the distance from the portion of the chemical structure 202'. Additionally, upon successful connection of the in-progress chemical structure 202 and the structure element 204, in some implementations, an audible feedback cue 214 may be provided to the user to indicate success. In other examples, the zoom pane 210 may portray the name of a completed molecular structure (if applicable), or the zoom panel may close until pending addition of another structure element or another modification of the in-progress chemical structure 202 is pending.

Figure 3A:
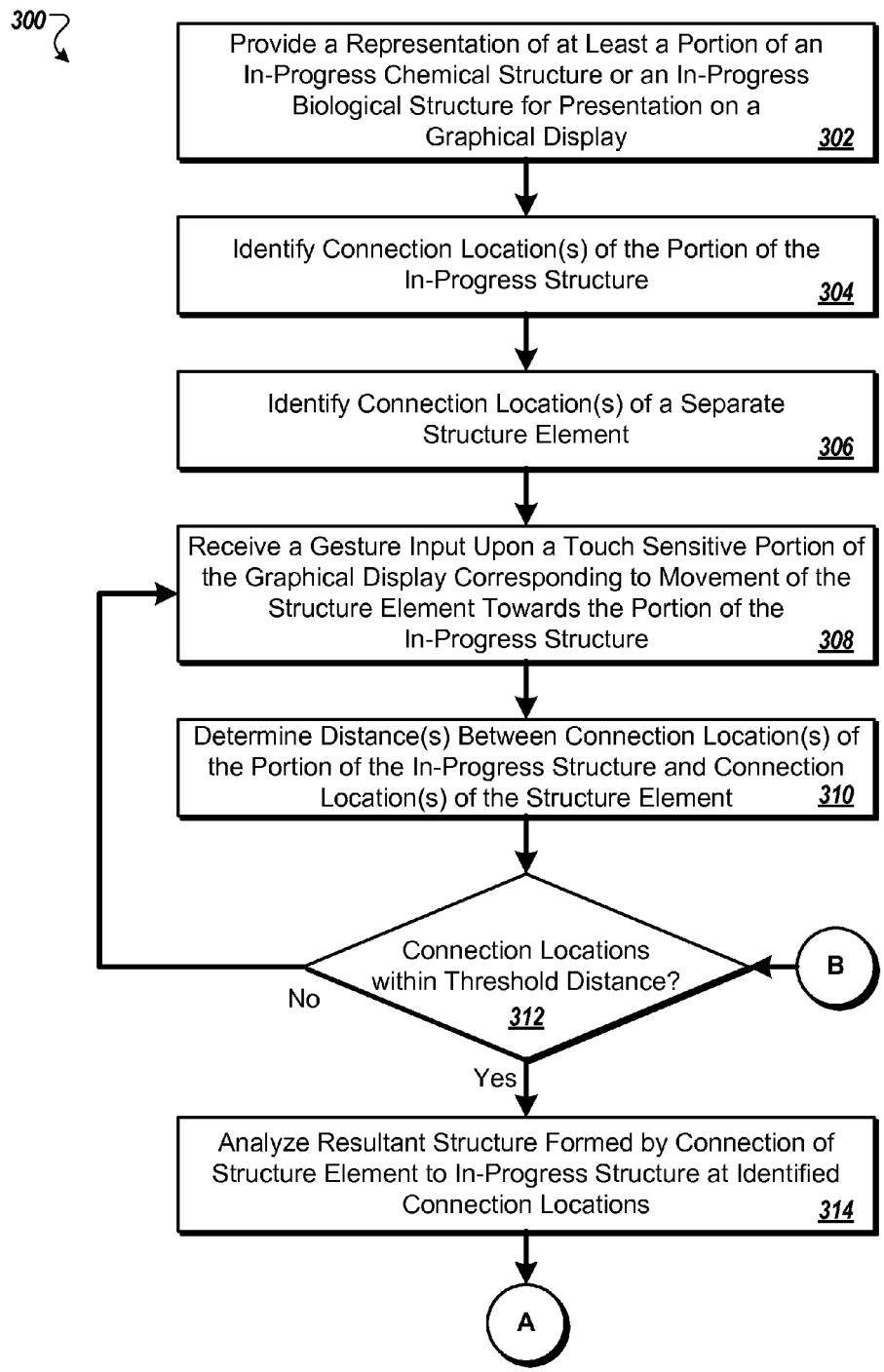
FIGS. 3A and 3B illustrate a flow chart of an example method for providing feedback cues during a gesture-based addition of an element to an in-progress structure drawing within a utility of creating or editing a graphical representation of a chemical structure or a biological structure.
Figure 3B:
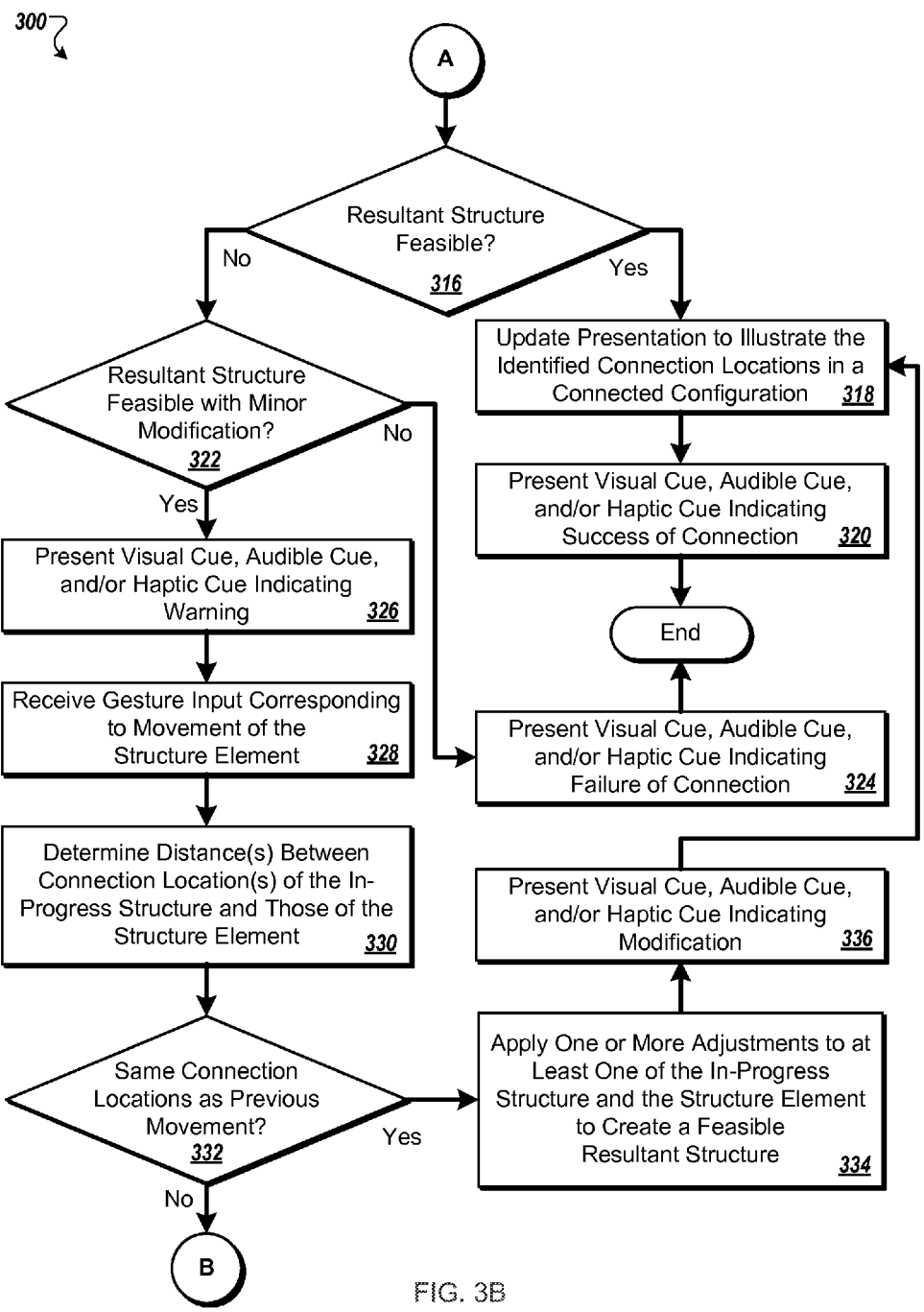

FIG. 3 is a flow chart of an example method 300 for providing feedback cues during a gesture-based addition of an element to an in-progress structure drawing within a utility for creating or editing a graphical representation of a chemical structure or biological structure. The method 300, for example, may be performed by a structure drawing/editing utility executing upon a touch screen computing device, such as a tablet computer, notebook computer, or smart phone.

In some implementations, the method 300 begins with providing a representation of at least a portion of an in-progress chemical structure or an in-progress biological structure for presentation on a graphical display (302). For example, as illustrated in relation to FIGS. 1A, 1B, 2A, and 2B, an in-progress chemical structure may be displayed within a chemical structure drawing/editing utility. The in-progress structure, in some examples, may include a two dimensional or three dimensional graphic representation of a chemical structure, a molecular structure, or a biological structure.

In some implementations, one or more connection locations are identified on the portion of the in-progress structure (304). A connection location may be, for example, an atom (e.g., a carbon or heteroatom on a hydrocarbon chain or ring of an in-progress structure which a selected structure element is to be attached to, replace, merge with, or subsume), a bond (e.g., a single, double, or triple bond of an in-progress structure which a bond of a selected structure element is to be attached to or replace, merge with, or subsume), a ring (e.g., a ring of an in-progress structure which a selected structure element is to be attached to or replace, merge with, or subsume), or other moiety of the in-progress structure which a selected structure element is to be attached to, replace, merge with, or subsume.

In some implementations, one or more connection locations are identified on a selected structure element separate from the in-progress structure (306). The structure element, in some examples, may be a molecule, atom, substituent, or biological scaffold. The structure element, in some implementations, includes one or more nucleotides, an amino acid residue, and/or or an amino acid. As identified above in relation to the connection locations of the in-progress structure, a connection location may be, for example, an atom (e.g., a carbon or heteroatom on a hydrocarbon chain or ring of an in-progress structure which a selected structure element is to be attached to, replace, merge with, or subsume), a bond (e.g., a single, double, or triple bond of an in-progress structure which a bond of a selected structure element is to be attached to or replace, merge with, or subsume), a ring (e.g., a ring of an in-progress structure which a selected structure element is to be attached to or replace, merge with, or subsume), or other moiety of the in-progress structure which a selected structure element is to be attached to, replace, merge with, or subsume.

In some implementations, a gesture corresponding to movement of the structure element towards the portion of the in-progress structure is received (308). The gesture, for example, may be input by a user upon a touch sensitive portion of the graphic display. In some examples, the gesture may include a drag, push, or "flinging" motion of the structure element towards the portion of the in-progress structure.

In some implementations, one or more distances between connection locations of the portion of the in-progress structure and connection locations of the structure element are determined (310). For example, the nearest pair(s) of respective connection locations of the in-progress structure and the structure element may be identified. The positions, for example, may be determined based upon mapping of pixel data to a screen area of the user device. Because screen sizes may vary, in some implementations, a relative distance is determined. In other implementations, an actual distance is determined. In some implementations, the distances are scaled in relation to a scale of the in-progress structure.

In some implementations, it is determined that two or more pairs of connection locations are within a threshold separation distance (312). In some implementations, the distance is established to one of "essentially touching" or "substantially overlapping". In other implementations, the threshold distance is a relative or absolute value used to determine intent of a user to connect the structure element to the in-progress structure at a particular pair (or, optionally, pairs) of connection locations. The threshold distance, in some implementations, may be based in part upon a type of in-progress chemical structure (e.g., two dimensional or three dimensional, biological, chemical, or molecular, etc.). In some implementations, the threshold distance may be based in part upon a type of structure element and/or a type of element corresponding to the identified connection location on the in-progress chemical structure. In a particular example, the threshold distance may be based on intermolecular forces, intramolecular forces, and/or van der Waal forces corresponding to the in-progress chemical structure and/or the structure element.

In some implementations, upon determining that connection locations are within a threshold distance (e.g., the user intends to connect the structure element to the in-progress structure at an identified connection location), a resultant structure formed by connection of the structure element to the in-progress structure at the identified connection locations is analyzed (314). According to the analysis, a determination may be made as to whether the resultant structure is chemically feasible. For example, based upon bond saturation at the connection location of the in-progress chemical structure, structure element may be prevented from attaching at the connection location due to steric hindrance, saturation, number of existing substituents at the connection location, etc.

In some implementations, if the resultant structure is identified as being feasible (316), a graphical presentation is updated to illustrate the identified connection locations in connected configuration (318). In one example, the illustration of connected locations is presented within a zoom pane, for example as described in relation to FIG. 2B. In another example, the structure element is automatically pulled towards the connection location of the in-progress structure (e.g., as though by magnetic force) to visually complete the connection.

Whether or not the graphical presentation is updated (318), in some implementations, a visual cue, audible cue, and/or haptic cue is presented to the user indicating success of connection (320). For example, if the connection locations were identified as already being overlapping or substantially overlapping, in some implementations, the graphical presentation may not be updated. However, based upon acceptance of the connection of the structure element to the in-progress structure at the connection location, one or more feedback cues may be provided to the user. In some examples, the feedback cue may include an audible cue (e.g., "click" of the structure element joining with the in-progress chemical structure, "ding" or other bell tone indicating success, fanfare sound, beep, etc.), a haptic cue (e.g., a "pull" of the structure element towards the chemical structure), and/or a visible cue (e.g., change of brightness, contrast, or background color of the display, modulation of display, confirmation animation within a zoom pane area, etc.).

If, instead, the resultant structure is identified as not being feasible (316), in some implementations, the resultant structure is further analyzed to determine if a feasible structure could be produced with one or more minor modifications (322). For example, should a replacement of a double bond with a single bond allow for a chemical structure element to attach to an in-progress chemical structure, the resultant structure may be determined to be feasible upon acceptance of modification.

In some implementations, if the resultant structure is not determined to be feasible even with one or more minor modifications (322), a feedback cue is presented indicating failure of connection between the in-progress structure and the structure element (320). For example, as described in relation to FIG. 1A, the connection attempted by the user via the gesture 112 may be prevented, and feedback cues such as a haptic repulsion of the gesture movement, a vibration, an audible warning tone, and/or a visual indication of failure (e.g., adjustment of background color, flashing, zoom pane warning of failure, etc.) may be presented to the user.

In addition to an indication of failure, in some implementations, an indication may be provided of an alternative connection location upon the in-progress structure. For example, upon the in-progress structure itself and/or within a separate zoom pane, a visual cue may be presented to the user indicating one or more connection locations that would result in a feasible structure.

In some implementations, based upon the resultant structure requiring minor modification, a feedback cue is presented indicating a warning (326). The warning feedback cue may be provided to the user such that the user is alerted that, although the attempted connection failed, the connection between the in-progress structure and the structure element at the connection may be allowed to complete upon additional attempt. In some examples, a warning feedback cue may include a weaker haptic repulsion than that of a failure cue, a weaker/shorter vibration, an audible warning tone, and/or a visual indication of warning (e.g., adjustment of background color, flashing, zoom pane warning of the need for modification to provide for connection at the identified connection location, etc.) may be presented to the user.

In some implementations, another gesture input corresponding to movement of the structure element is received (328). The gesture, for example, may be input by a user upon a touch sensitive portion of the graphic display. In some examples, the gesture may include a drag, push, or "flinging" motion of the structure element towards the portion of the in-progress structure.

In some implementations, one or more distances between connection locations of the portion of the in-progress structure and connection locations of the structure element are determined (330). For example, distances may be determined as described above in relation to step 310.

In some implementations, if the same connection locations are identified as being within a threshold distance of each other as previously (e.g., in relation to step 312) (332), one or more adjustments are automatically applied to at least one of the in-progress structure and the structure element to create a feasible resultant structure (334). For example, one or more atoms, bonds, rings, chains, moieties, or other substituents may be removed from the in-progress chemical structure, or appropriately altered, to provide for addition of the structural element. In a particular example, a double bond may be converted to a single bond to allow for attachment of a substituent.

In some implementations, a feedback cue is presented to the user indicating a modification was made to one or both of the in-progress chemical structure and the structure element to provide for a feasible resultant structure (336). For example, as illustrated in relation to FIG. 2B, loss of elements from one or both of the in-progress structure and the structure element may be illustrated within a zoom pane animation. In another example, a scrolling message presented in a region of the graphic display separate from the main creating/editing pane may describe to the user modifications made to the in-progress structure and/or structure element.

In some implementations, the user is provided with an undo operation configured, upon selection, to return to the state of the in-progress chemical structure prior to modification. For example, a visual feedback cue may identify an option (e.g., selectable control, gesture input, verbal command, etc.) for backing out any modifications automatically made in the effort to support the connection of the structure element to the in-progress chemical structure. A timer may be associated with the undo operation. For example, a user may be supplied with a period of time prior to the modifications becoming permanent (e.g., incapable of being automatically backed out of the in-progress chemical structure). A "waiting tone" or other audible and/or visual cue may alert the user to the passing of time prior to commitment of the modification.

In some implementations, the graphical presentation is updated to illustrate the connection locations in a connected configuration (318) and a feedback cue is presented to the user indicating success of connection (320), as described above.

In some implementations, the various haptic, audible, and/or visual feedback cues may be set in part via user options. For example, a user preferences menu of a structure drawing/editing utility may provide audible cue options (e.g., selection of various tones, volume settings, tone durations, etc.), visual cue options (e.g., enable/disable zoom pane, flash screen, present feedback message in scrolling region outside main display pane, etc.), and/or haptic cue options (e.g., enable haptic cues, haptic cue strength, haptic cue durations, enable vibration cue, etc.). In some implementations, various cues may be refined such that a different cue setting is applicable based upon a type of structure element or a type of connection between the structure element and the in-progress structure. For example, cue settings may be specific to atom type or bond type in the structure element or in-progress structure at or near the connection location, and/or the cue setting may be specific to connection type, number or type of replaced atoms or bonds required for creating the resultant structure, etc.

Although described in relation to response to movements of structure elements by a user via a touch screen interface, in other implementations, a portion of the method 300 may be applied to chemical reaction simulations to apply feedback cues (e.g., visual, audible, or haptic) corresponding to chemical structure interaction during the chemical reactions. Alternatively or additionally, a portion of the method 300 may be applied to molecular dynamics simulations to apply feedback cues (e.g., visual, audible, or haptic) corresponding to molecular interactions between two or more species in a mixture, solution, etc.

Figure 4:
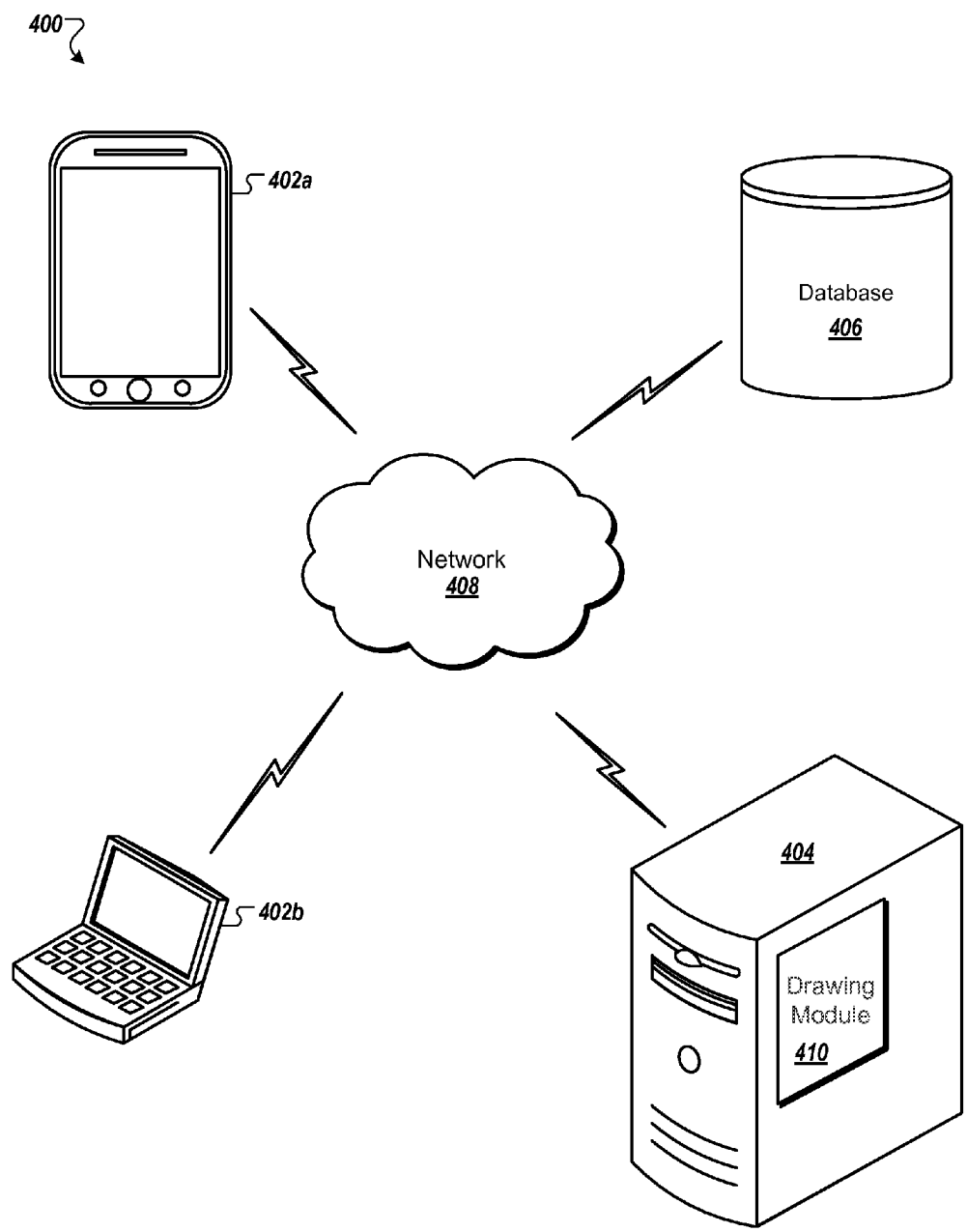
FIG. 4 is a schematic diagram of an example system for drawing or editing chemical structures.

FIG. 4 depicts an example system 400 for drawing or editing graphical representations of chemical structures. The system 400 includes client nodes 402a and 402b, a server node 404, a database 406, and, for enabling communications therebetween, a network 408. As illustrated, the server node 404 may include a drawing module 410.

The network 408 may be, for example, a local-area network (LAN), such as a company or laboratory Intranet, a metropolitan area network (MAN), or a wide area network (WAN), such as the Internet. Each of the client nodes 402, server node 404, and the database 406 may be connected to the network 408 through a variety of connections including, but not limited to, standard telephone lines, LAN or WAN links (e.g., T1, T3, 56 kb, X.25), broadband connections (e.g., ISDN, Frame Relay, ATM), or wireless connections. The connections, moreover, may be established using a variety of communication protocols (e.g., HTTP, TCP/IP, IPX, SPX, NetBIOS, NetBEUI, SMB, Ethernet, ARCNET, Fiber Distributed Data Interface (FDDI), RS232, IEEE 802.11, IEEE 802.11a, IEEE 802.11b, IEEE 802.11g, and direct asynchronous connections).

The client node 402a may be any type of wireless device, information appliance, tablet computer, personal digital assistant, cellular phone, handheld device, or other portable computing device that is capable of both presenting information/data to, and receiving commands from, a user of the client node 402a (e.g., an analytical chemist). Similarly, the client node 402b may be any type of personal computer, Windows-based terminal, network computer, wireless device, information appliance, RISC Power PC, X-device, workstation, mini computer, main frame computer, set top box, or other computing device that is capable of both presenting information/data to, and receiving commands from, a user of the client node 402b. The client nodes 402 may include, for example, a graphical display device (e.g., a touch screen or a computer monitor), a data entry device (e.g., a keyboard, a touch screen, or a mouse pad), persistent and/or volatile storage (e.g., computer memory), and a processor. In one embodiment, the client node 402 includes a web browser, such as, for example, Internet Explorer® developed by Microsoft Corporation of Redmond, Wash., to connect to the World Wide Web.

For its part, the server node 404 may be any computing device that is capable of receiving information/data from and delivering information/data to the client nodes 402, for example over the network 408, and that is capable of querying, receiving information/data from, and delivering information/data to the server node 404. For example, as further explained below, the server node 404 may receive input (e.g., a touch gesture) from a user of the client node 402, create or edit a chemical structure representation according to the input, and present or display the chemical structure representation to the user at the client node 402. The server node 404 may include a processor and persistent and/or volatile storage, such as computer memory.

The server node 404 may be any computing device that is capable of storing and managing collections of data, such as data relating to chemical structure representations. The chemical structure representations may be, for example, of the type described in related U.S. Pat. No. 8,433,723, filed May 3, 2011, titled "Systems, Methods, and Apparatus for Processing Documents to Identify Structures," related U.S. application Ser. No. 13/239,069, filed Sep. 21, 2011, titled "Systems, Methods, and Apparatus for Facilitating Chemical Analyses," related International Patent Application No. PCT/US12/26574, filed Feb. 24, 2012, titled "Systems, Methods, and Apparatus for Drawing Chemical Structures Using Touch and Gestures," U.S. application Ser. No. 13/714,312, filed Dec. 13, 2012, titled "Draw-Ahead Feature for Biological Sequence Drawing Applications," and U.S. application Ser. No. 13/714,307, filed Dec. 13, 2012, titled "Draw-Ahead Feature for Chemical Structure Drawing Applications," the disclosures of each of which are hereby incorporated by reference herein in their entireties.

As used herein, the term "server node" is broadly used to refer to any repository of information. The data stored within the server node 404 may be harvested from the server node 404 in any manner. In one embodiment, the harvesting is performed utilizing indexing and structure recognition algorithms, and the harvested data is connected together by examining and correlating the disjointed information that is found.

The drawing module 410 of the server node 404 may be implemented as any software program and/or hardware device, for example an application specific integrated circuit (ASIC) or a field programmable gate array (FPGA), that is capable of providing the functionality described herein. It will be understood by one having ordinary skill in the art, however, that the illustrated module 410, and the organization of the server node 404, are conceptual, rather than explicit, requirements. For example, it should be understood that the drawing module 410 may in fact be implemented as multiple modules, such that the functions performed by the single module, as described herein, are in fact performed by the multiple modules.

Although not shown in FIG. 4, any or all of the client nodes 402, the server node 404, and the database 406 may also include its own transceiver (or separate receiver and transmitter) that is capable of receiving and transmitting communications, including requests, responses, and commands, such as, for example, inter-processor communications and networked communications. The transceivers (or separate receivers and transmitters) may each be implemented as a hardware device, or as a software module with a hardware interface.

It will also be understood by those skilled in the art that FIG. 4 is a simplified illustration of the system 400 and that it is depicted as such to facilitate the explanation of various embodiments of the present disclosure. Moreover, the system 400 may be modified in a variety of manners without departing from the spirit and scope of the present disclosure. For example, rather than being implemented on a single server node 404, the drawing module 410 may instead be implemented on a different computing device (not shown) and such computing devices may communicate with one another directly, over the network 408, or over another additional network (not shown). In yet another example, the functionality of the server node 404 may in fact be resident on the server node 404 (e.g., be implemented in the computer memory thereof). Additional options are for the server node 404 and/or the database 406 to be local to the client node 402 (such that they may all communicate directly without using the network 408), or for the functionality of the server node 404 and/or the database 406 to be implemented on the client node 402 (e.g., for the drawing module 410 and/or the server node 404 to reside on the client node 402). As such, the depiction of the system 400 in FIG. 4 is non-limiting.

In certain embodiments, the system 400 allows a user to draw and edit a chemical structure representation using one or more fingers on an input interface, such as a touch pad or touch screen, at the client tablet node 402*a*. The system 400, in some embodiments, allows a user to draw and edit a graphical representation of a chemical structure using a mouse, stylus, keypad, trackball, or other input interface, such as an input interface at a client personal computer 402*b*. The input interface, in some implementations, may include a natural language processing module capable of converting utterances to a series of commands for activating controls of the user interface.

In general, the drawing module 410 in the server node 404 is configured to draw or revise the chemical structure representation according to the input from the user, as explained above with respect to the prior figures. The drawing module 410 may then provide an image (e.g., a collection of pixels) of the graphical representation of the chemical structure for presentation to the user on the graphical display of the particular client node 402. Additionally, the drawing module 410 may provide audio, visual, and/or haptic cues related to potential amendment to a graphical representation of a chemical structure. The feedback cues, for example, may be related to a result of analysis of a resultant chemical structure formed from the addition of a structure element to an in-progress chemical structure. In general, the system 400 may be used to perform any of the methods described herein.

Figure 5:
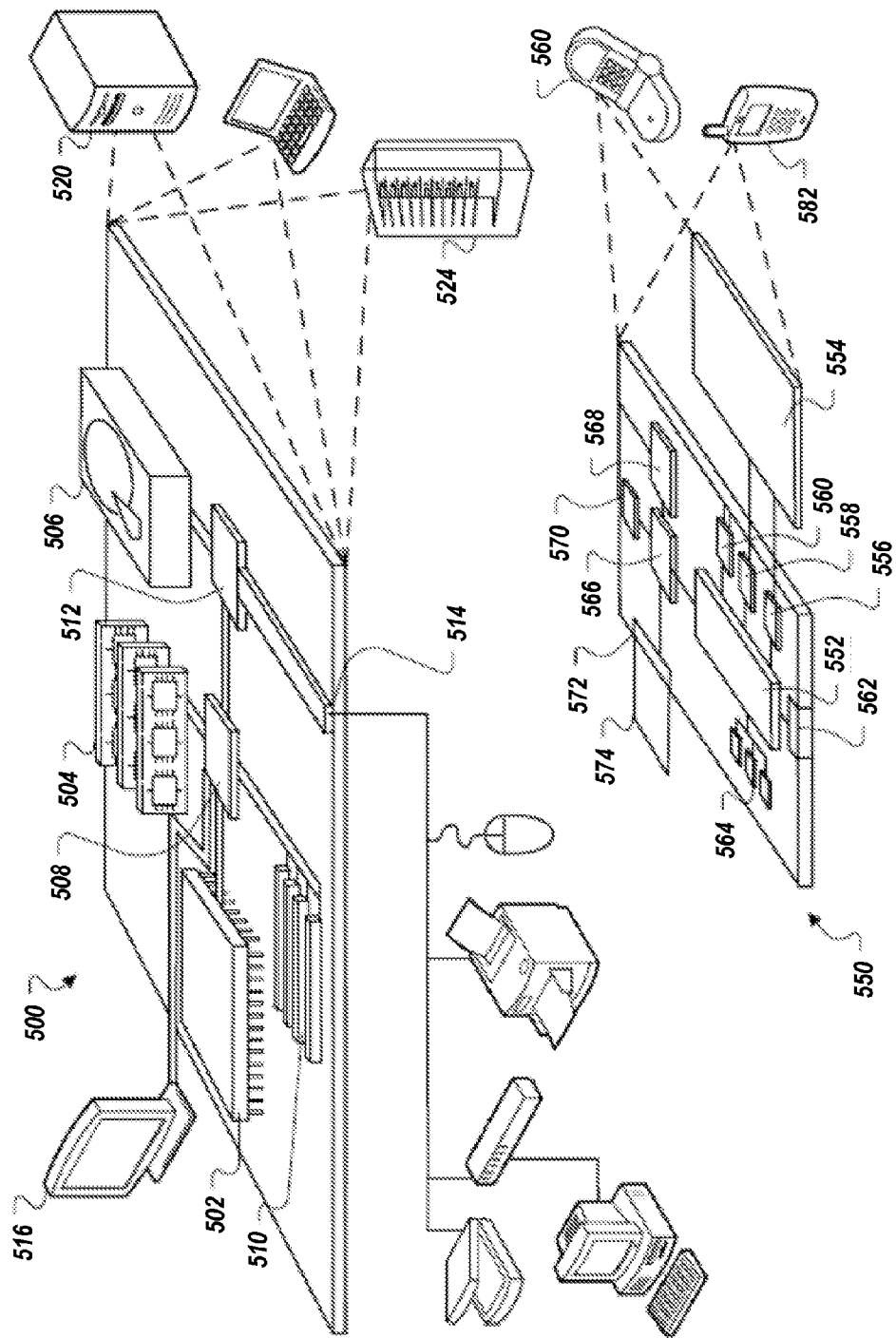
FIG. 5 is a block diagram of an example computing device and an example mobile computing device.

FIG. 5 shows an example of a computing device 500 and a mobile computing device 550 that can be used to implement the techniques described in this disclosure. The computing device 500 is intended to represent various forms of digital computers, such as laptops, desktops, workstations, personal digital assistants, servers, blade servers, mainframes, and other appropriate computers. The mobile computing device 550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 500 includes a processor 502, a memory 504, a storage device 506, a high-speed interface 508 connecting to the memory 504 and multiple high-speed expansion ports 510, and a low-speed interface 512 connecting to a low-speed expansion port 514 and the storage device 506. Each of the processor 502, the memory 504, the storage device 506, the high-speed interface 508, the high-speed expansion ports 510, and the low-speed interface 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as a display 516 coupled to the high-speed interface 508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 504 stores information within the computing device 500. In some implementations, the memory 504 is a volatile memory unit or units. In some implementations, the memory 504 is a non-volatile memory unit or units. The memory 504 may also be another form of computer-readable medium, such as a magnetic or optical disk.

The storage device 506 is capable of providing mass storage for the computing device 500. In some implementations, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 502), perform one or more methods, such as those described above. The instructions can also be stored by one or more storage devices such as computer- or machine-readable mediums (for example, the memory 504, the storage device 506, or memory on the processor 502).

The high-speed interface 508 manages bandwidth-intensive operations for the computing device 500, while the low-speed interface 512 manages lower bandwidth-intensive operations. Such allocation of functions is an example only. In some implementations, the high-speed interface 508 is coupled to the memory 504, the display 516 (e.g., through a graphics processor or accelerator), and to the high-speed expansion ports 510, which may accept various expansion cards (not shown). In the implementation, the low-speed interface 512 is coupled to the storage device 506 and the low-speed expansion port 514. The low-speed expansion port 514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. In addition, it may be implemented in a personal computer such as a laptop computer 522. It may also be implemented as part of a rack server system 524. Alternatively, components from the computing device 500 may be combined with other components in a mobile device (not shown), such as a mobile computing device 550. Each of such devices may contain one or more of the computing device 500 and the mobile computing device 550, and an entire system may be made up of multiple computing devices communicating with each other.

The mobile computing device 550 includes a processor 552, a memory 564, an input/output device such as a display 554, a communication interface 566, and a transceiver 568, among other components. The mobile computing device 550 may also be provided with a storage device, such as a micro-drive or other device, to provide additional storage. Each of the processor 552, the memory 564, the display 554, the communication interface 566, and the transceiver 568, are interconnected using various buses, and several of the components may be mounted on a common motherboard or in other manners as appropriate.

The processor 552 can execute instructions within the mobile computing device 550, including instructions stored in the memory 564. The processor 552 may be implemented as a chipset of chips that include separate and multiple analog and digital processors. The processor 552 may provide, for example, for coordination of the other components of the mobile computing device 550, such as control of user interfaces, applications run by the mobile computing device 550, and wireless communication by the mobile computing device 550.

The processor 552 may communicate with a user through a control interface 558 and a display interface 556 coupled to the display 554. The display 554 may be, for example, a TFT (Thin-Film-Transistor Liquid Crystal Display) display or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may provide communication with the processor 552, so as to enable near area communication of the mobile computing device 550 with other devices. The external interface 562 may provide, for example, for wired communication in some implementations, or for wireless communication in other implementations, and multiple interfaces may also be used.

The memory 564 stores information within the mobile computing device 550. The memory 564 can be implemented as one or more of a computer-readable medium or media, a volatile memory unit or units, or a non-volatile memory unit or units. An expansion memory 574 may also be provided and connected to the mobile computing device 550 through an expansion interface 572, which may include, for example, a SIMM (Single In Line Memory Module) card interface. The expansion memory 574 may provide extra storage space for the mobile computing device 550, or may also store applications or other information for the mobile computing device 550. Specifically, the expansion memory 574 may include instructions to carry out or supplement the processes described above, and may include secure information also. Thus, for example, the expansion memory 574 may be provide as a security module for the mobile computing device 550, and may be programmed with instructions that permit secure use of the mobile computing device 550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 552), perform one or more methods, such as those described above. The instructions can also be stored by one or more storage devices, such as one or more computer- or machine-readable mediums (for example, the memory 564, the expansion memory 574, or memory on the processor 552). In some implementations, the instructions can be received in a propagated signal, for example, over the transceiver 568 or the external interface 562.

The mobile computing device 550 may communicate wirelessly through the communication interface 566, which may include digital signal processing circuitry where necessary. The communication interface 566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 568 using a radio-frequency. In addition, short-range communication may occur, such as using a Bluetooth®, Wi-Fi™, or other such transceiver (not shown). In addition, a GPS (Global Positioning System) receiver module 570 may provide additional navigation- and location-related wireless data to the mobile computing device 550, which may be used as appropriate by applications running on the mobile computing device 550.

The mobile computing device 550 may also communicate audibly using an audio codec 560, which may receive spoken information from a user and convert it to usable digital information. The audio codec 560 may likewise generate audible sound for a user, such as through a speaker, e.g., in a handset of the mobile computing device 550. Such sound may include sound from voice telephone calls, may include recorded sound (e.g., voice messages, music files, etc.) and may also include sound generated by applications operating on the mobile computing device 550.

The mobile computing device 550 may be implemented in a number of different forms, as shown in the figure. For example, it may be implemented as a cellular telephone 580. It may also be implemented as part of a smart-phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

It should also be noted that embodiments of the present disclosure may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or Java. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

In view of the structure, functions and apparatus of the systems and methods described here, in some implementations, systems and methods for creating graphical representations of chemical structures and/or biological structures via a touch interface with feedback cues are provided. Having described certain implementations of methods and apparatus for providing feedback cues for touch screen interaction with chemical structure or biological structure drawing applications, it will now become apparent to one of skill in the art that other implementations incorporating the concepts of the disclosure may be used. Therefore, the disclosure should not be limited to certain implementations, but rather should be limited only by the spirit and scope of the following claims.

The invention claimed is:

1. A system for creating a graphical representation of at least one of a chemical structure and a biological structure using a touch screen interface, the system comprising:
   a processor; and
   a memory having a set of instructions stored thereon, wherein the instructions, when executed, cause the processor to:
   provide a representation of at least a portion of an in-progress chemical or biological structure for presentation on a graphical display of a computing device;
   identify one or more connection locations of the portion of the in-progress chemical or biological structure;
   identify one or more connection locations of a chemical or biological structure element, wherein the chemical or biological structure element is separate from the in-progress chemical or biological structure;
   receive a gesture input upon a touch sensitive portion of the graphical display corresponding to movement of the chemical or biological structure element towards the portion of the in-progress chemical or biological structure, wherein the gesture input comprises a motion selected from the group consisting of drag, push, fling, or any combination thereof;
   determine whether a distance between a first connection location of the one or more connection locations of the portion of the in-progress chemical or biological structure and a first connection location of the one or more connection locations of the chemical or biological structure element is within a threshold separation distance that signals an intended connection of the chemical or biological structure element to the in-progress chemical or biological structure at or about the corresponding connection locations;
   determine the intended connection between the first connection location of the one or more connection locations of the portion of the in-progress chemical or biological structure and the first connection location of the one or more connection locations of the chemical or biological structure element;
   based upon determining the intended connection, analyze a resultant chemical or biological structure formed by connection of the in-progress chemical or biological structure and the chemical or biological structure element at or about the corresponding connection locations of the chemical or biological structure element and the in-progress chemical or biological structure, to determine whether the resultant structure is chemically or biologically feasible;
   provide, responsive to the analysis, for presentation to a user of the computing device, a visible cue and optionally one or more of an audible cue and a haptic cue, based on the determination that the resultant chemical or biological structure is chemically or biologically feasible;
   present, within the graphical display, a formation of the resultant chemical or biological structure; and
   present, to the user, the visible cue of the first connection location of the chemical or biological structure element connecting with the first connection location of the in-progress chemical or biological structure, wherein the visible cue comprises a visible indication of a loss of one or more atoms caused by the formation of the resultant chemical or biological structure.

2. The system of claim 1, wherein at least one of i) a strength of the haptic cue, ii) a duration of the haptic cue, iii) a volume of the audible cue, iv) a duration of the audible cue, and v) a tone of the audible cue is selected based at least in part upon the determination that the resultant chemical or biological structure is chemically or biologically feasible.

3. The system of claim 1, wherein at least one of i) a strength of the haptic cue, ii) a duration of the haptic cue, iii) a volume of the audible cue, iv) a duration of the audible cue, and v) a tone of the audible cue is selected based at least in part upon a number of bonds formed between a) the first connection location of the chemical or biological structure element and b) the first connection location of the in-progress chemical or biological structure.

4. The system of claim 1, wherein the visible cue comprises a zoom display panel presented upon the graphical display.

5. The system of claim 1, wherein the instructions, when executed, cause the processor to append the chemical or biological structure element to the in-progress chemical or biological structure at the corresponding connection locations.

6. The system of claim 1, wherein the instructions, when executed, cause the processor to replace a portion of the in-progress chemical or biological structure with at least a portion of the chemical or biological structure element at the corresponding connection locations.

7. The system of claim 1 wherein the instructions, when executed, cause the processor to merge the chemical or biological structure element into the in-progress chemical or biological structure at the corresponding connection locations.

8. The system of claim 1, wherein the visible cue comprises an alteration in at least one of color, brightness, and contrast of at least a portion of the graphical display.

9. The system of claim 1, wherein receiving the gesture input comprises receiving the gesture input, over a network, from the computing device.

10. The system of claim 1, wherein the computing device comprises the processor.

11. A method comprising:
providing a representation of at least a portion of an in-progress chemical or biological structure for presentation on a graphical display of a computing device;
identifying, by a processor of a computing device, one or more connection locations of the portion of the in-progress chemical or biological structure;
identifying, by the processor, one or more connection locations of a chemical or biological structure element, wherein the chemical or biological structure element is separate from the in-progress chemical or biological structure;
receiving a gesture input upon a touch sensitive portion of the graphical display corresponding to movement of the chemical or biological structure element towards the portion of the in-progress chemical or biological structure, wherein the gesture input is a motion selected from the group consisting of drag, push, filing, or any combination thereof;
determining, by the processor, whether a distance between a first connection location of the one or more connection locations of the portion of the in-progress chemical or biological structure and a first connection location of the one or more connection locations of the chemical or biological structure element is within a threshold separation distance that signals an intended connection of the chemical or biological structure element to the in-progress chemical or biological structure at or about the corresponding connection locations;
determining, by the processor, the intended connection between the first connection location of the one or more connection locations of the portion of the in-progress chemical or biological structure and the first connection location of the one or more connection locations of the chemical or biological structure element;
based upon determining the intended connection, analyzing, by the processor, a resultant chemical or biological structure formed by connection of the in-progress chemical or biological structure and the chemical or biological structure element at or about the corresponding connection locations of the chemical or biological structure element and the in-progress chemical or biological structure to determine whether the resultant structure is chemically or biologically feasible;
providing, responsive to the analysis, for presentation to a user of the computing device, a feedback cue, wherein the feedback cue comprises a visible cue and optionally one or more of an audible cue and a haptic cue, based on the determination that the resultant chemical or biological structure is chemically or biologically feasible;
presenting, within the graphical display, a formation of the resultant chemical or biological structure; and
presenting, to the user, the visible cue of the first connection location of the chemical or biological structure element connecting with the first connection location of the in-progress chemical or biological structure,
wherein the visible cue comprises a visible indication of a loss of one or more atoms caused by the formation of the resultant chemical or biological structure.

12. The method of claim 11, wherein the feedback cue is selected based at least in part upon at least one of a) a type of the chemical or biological structure element and b) a type of an element of the in-progress chemical or biological structure comprising the first connection location.

13. The method of claim 12, wherein the type of the chemical or biological structure element is a molecule, an atom, or a substituent.

14. The method of claim 12, wherein the in-progress chemical or biological structure is a biological sequence.

15. The method of claim 14, wherein the type of the structure element is a biological scaffold.

16. The method of claim 14, wherein the structure element comprises one or more nucleotides.

17. The method of claim 14, wherein the structure element comprises at least one of an amino acid residue or amino acid.

18. A non-transitory computer readable medium having instructions stored thereon, wherein the instructions, when executed by a processor, cause the processor to:
provide a representation of at least a portion of an in-progress chemical or biological structure for presentation on a graphical display of a computing device;
identify one or more connection locations of the portion of the in-progress chemical or biological structure;
identify one or more connection locations of a chemical or biological structure element, wherein the chemical or biological structure element is separate from the in-progress chemical or biological structure;

receive a gesture input upon a touch sensitive portion of the graphical display corresponding to movement of the chemical or biological structure element towards the portion of the in-progress chemical or biological structure, wherein the gesture input comprises a motion selected from the group consisting of drag, push, filing, or any combination thereof;

determine whether a distance between a first connection location of the one or more connection locations of the portion of the in-progress chemical or biological structure and a first connection location of the one or more connection locations of the chemical or biological structure element is within a threshold separation distance that signals an intended connection of the chemical or biological structure element to the in-progress chemical or biological structure at or about the corresponding connection locations;

determine the intended connection between the first connection location of the one or more connection locations of the portion of the in-progress chemical or biological structure and the first connection location of the one or more connection locations of the chemical or biological structure element, based upon determining the intended connection, analyze a resultant chemical or biological chemical or biological structure formed by connection of the in-progress chemical or biological structure and the chemical or biological structure element at or about the corresponding connection locations of the chemical or biological structure element and the in-progress chemical or biological structure to determine whether the resultant chemical or biological structure is chemically or biologically feasible;

provide, responsive to the analysis, for presentation to a user of the computing device, a visible cue and optionally one or more of an audible cue and a haptic cue, based on the determination that the resultant structure is chemically or biologically feasible;

present, within the graphical display, a formation of the resultant chemical or biological structure; and present, to the user, the visible cue of the first connection location of the chemical or biological structure element connecting with the first connection location of the in-progress chemical or biological structure, wherein the visible cue comprises a visible indication of a loss of one or more atoms caused by the formation of the resultant chemical or biological structure.

19. The non-transitory computer readable medium of claim 18, wherein the instructions cause the processor to, prior to determining whether the distance between the first connection location of the in-progress chemical or biological structure and the first connection location of the chemical or biological structure element signals the intended connection, for each connection location of the one or more connection locations of the chemical or biological structure element, and for each connection location of the one or more connection locations of the in-progress chemical or biological structure, determine a respective distance between the respective connection location of the chemical or biological structure element and the respective connection location of the in-progress chemical or biological structure, and identify whether the respective distance is within a threshold distance.

20. The non-transitory computer readable medium of claim 19, wherein the threshold distance is based at least in part upon a type of the in-progress chemical or biological structure.

21. The non-transitory computer readable medium of claim 19, wherein the threshold distance is based at least in part on one or more of intermolecular forces, intramolecular forces, and van der Waal forces corresponding to one or both of the in-progress chemical or biological structure and the chemical or biological structure element.

* * * * *